United States Patent
Jung

(10) Patent No.: US 6,433,215 B1
(45) Date of Patent: *Aug. 13, 2002

(54) 8-ALKYL-8-TRICYCLODECANYL (METH) ACRYLATE AND METHOD OF PRODUCING THE SAME

(75) Inventor: Hyun-jin Jung, Seoul (KR)

(73) Assignee: Chem Search Corp., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 09/516,611

(22) Filed: Mar. 1, 2000

(30) Foreign Application Priority Data

Feb. 19, 2000 (KR) ................................. 00-8035

(51) Int. Cl.[7] .......................... C07C 69/74; C07C 69/52
(52) U.S. Cl. ........................................ 560/220; 560/120
(58) Field of Search .................... 560/120, 220

(56) References Cited

U.S. PATENT DOCUMENTS 6,153,785 A * 11/2000 Jung ........................... 560/120

FOREIGN PATENT DOCUMENTS

JP 08240881 * 1/1996

* cited by examiner

*Primary Examiner*—Paul J. Killos
*Assistant Examiner*—Taylor V. Oh

(57) ABSTRACT

A novel tricyclodecanyl (meth)acrylate compound and a method of producing the same are provided. The compound is 8-alkyl-8-tricyclodecanyl (meth)acrylate represented by formula (1):

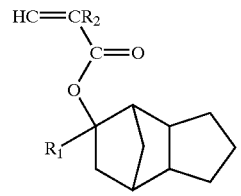

wherein $R_1$ is methyl or ethyl and $R_2$ is hydrogen or methyl.

3 Claims, 2 Drawing Sheets

8-ALKYL-8-TRICYCLODECANYL (METH) ACRYLATE AND METHOD OF PRODUCING THE SAME

BACKGROUND OF THE INVENTION

1. Field of the Invention

The present invention relates to a novel tricyclodecanyl (meth)acrylate compound and a method of producing the same, and more particularly, to 8-alkyl-8-tricyclodecanyl (meth)acrylates and a method of producing the same.

2. Description of the Related Art

Acrylates or methacrylates are useful monomers which are polymerized solely or copolymerized with other monomers to provide various kinds of polymers exhibiting excellent performance. The thus-produced polymers generally have excellent weather resistance and transparency. Also, according to the kinds of ester substituents, polymers of various performance levels can be produced. Specifically, in the case where the ester substituent is a bulky alicyclic compound which has low chemical reactivity, the polymers can be commercially used as various flame retardants and much attention is being paid to the production thereof.

However, conventional (meth) acrylate compounds having a bulky alicyclic substituent are cumbersome in view of reaction conditions, resulting in poor yield, and the purification thereof is difficult. Thus, it is quite difficult to produce the conventional (meth)acrylate compounds on a commercial scale.

SUMMARY OF THE INVENTION

To solve the above problems, it is an object of the present invention to provide an acrylate compound having a bulky substituent which can be produced and purified by a simplified process to be suitable for commercial-scale production.

It is another object of the present invention to provide a method for producing the acrylate compound.

Accordingly, to achieve the first object, there is provided 8-alkyl-8-tricyclodecanyl (meth)acrylate represented by formula (1):

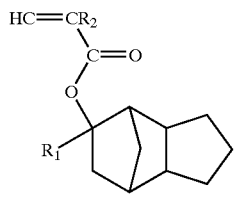

wherein $R_1$ is methyl or ethyl and $R_2$ is hydrogen or methyl.

To achieve the second object, there is provided a method of producing the compound including the steps of a) synthesizing 8-alkyl-8-tricyclodecanol by reacting tricyclodecan-8-one with either an alkyl Grignard reagent or an alkyl lithium reagent, and b) synthesizing 8-ethyl-8-tricyclodecanyl acrylate by reacting the 8-alkyl-8-tricyclodecanol synthesized in the step a) with (meth) acryloyl chloride.

Preferably, the Grignard reagent is either alkyl magnesium bromide or alkyl magnesium chloride.

More preferably, if the alkyl is ethyl, ethyl magnesium bromide or ethyl magnesium chloride is used as the Grignard reagent.

In the production method of the acrylate compound according to the present invention, a separation process may be performed after each step is completed. However, the separation process may be performed after all steps are performed in situ.

BRIEF DESCRIPTION OF THE DRAWINGS

The above objects and advantages of the present invention will become more apparent by describing in detail a preferred embodiment thereof with reference to the attached drawings in which.

DESCRIPTION OF THE PREFERRED EMBODIMENTS

Figure 1:
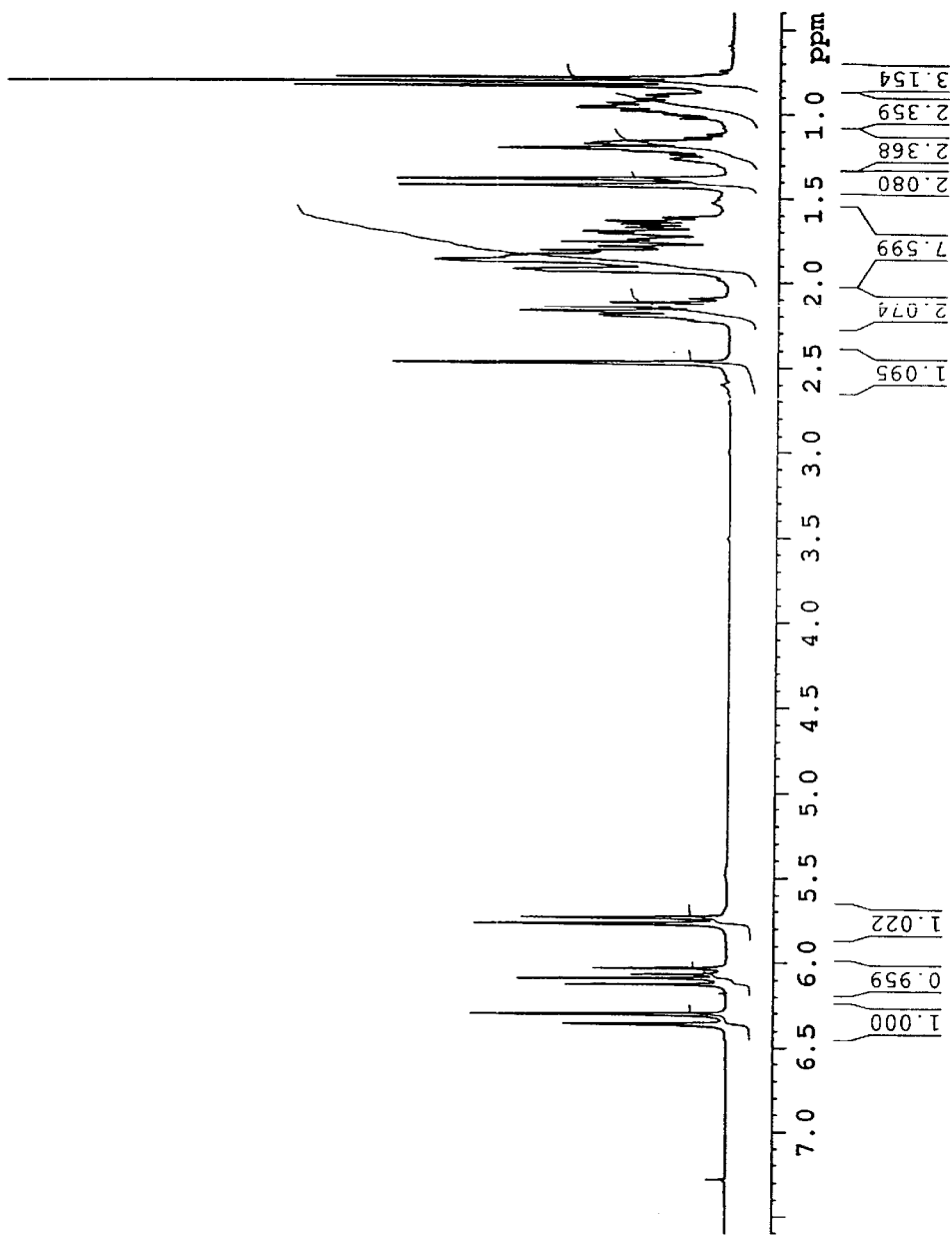
FIG. 1 is an NMR spectrum of 8-ethyl-8-tricyclodecanyl acrylate produced in Example 1 of the present invention.

A process for producing 8-alkyl-8-tricyclodecanyl (meth) acrylate according to the present invention will now be described in detail.

As shown in the following reaction scheme (1), tricyclodecan-8-one and an alkyl Grignard reagent or an alkyl lithium reagent are reacted, thereby synthesizing 8-alkyl-8-tricyclodecanol.

[Reaction scheme (1)]

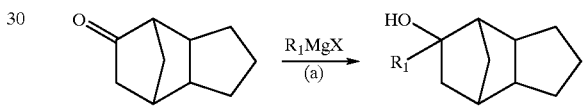

wherein $R_1$ is methyl or ethyl, and X is Cl or Br.

In view of side reaction inhibition and reaction yield, if 8-ethyl-8-tricyclodecanyl (meth)acrylate is a desired compound, ethyl magnesium bromide or ethyl magnesium chloride is preferably used as a Grignard reagent.

Since the above-described reaction is carried out by a general Grignard reaction mechanism, the reaction temperature and pressure are meaningless in the present invention.

Next, as shown in the following reaction scheme (2), 8-alkyl-8-tricyclodecanol and (meth)acryloyl chloride are reacted to synthesize 8-alkyl-8-tricyclodecanyl (meth) acrylate.

[Reaction scheme (2)]

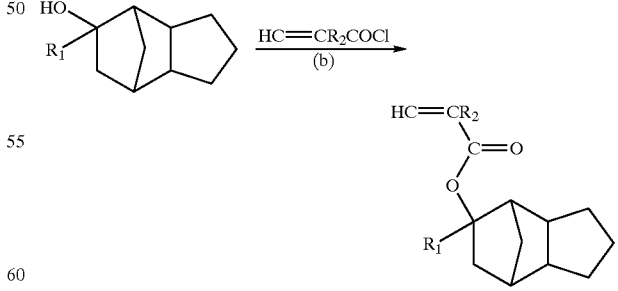

wherein $R_1$ is the same as defined as above and $R_2$ is hydrogen or methyl.

The present invention is described in more detail below by referring to the following examples, and the examples are intended to illustrate but not limit the invention.

EXAMPLE 1

Figure 2:
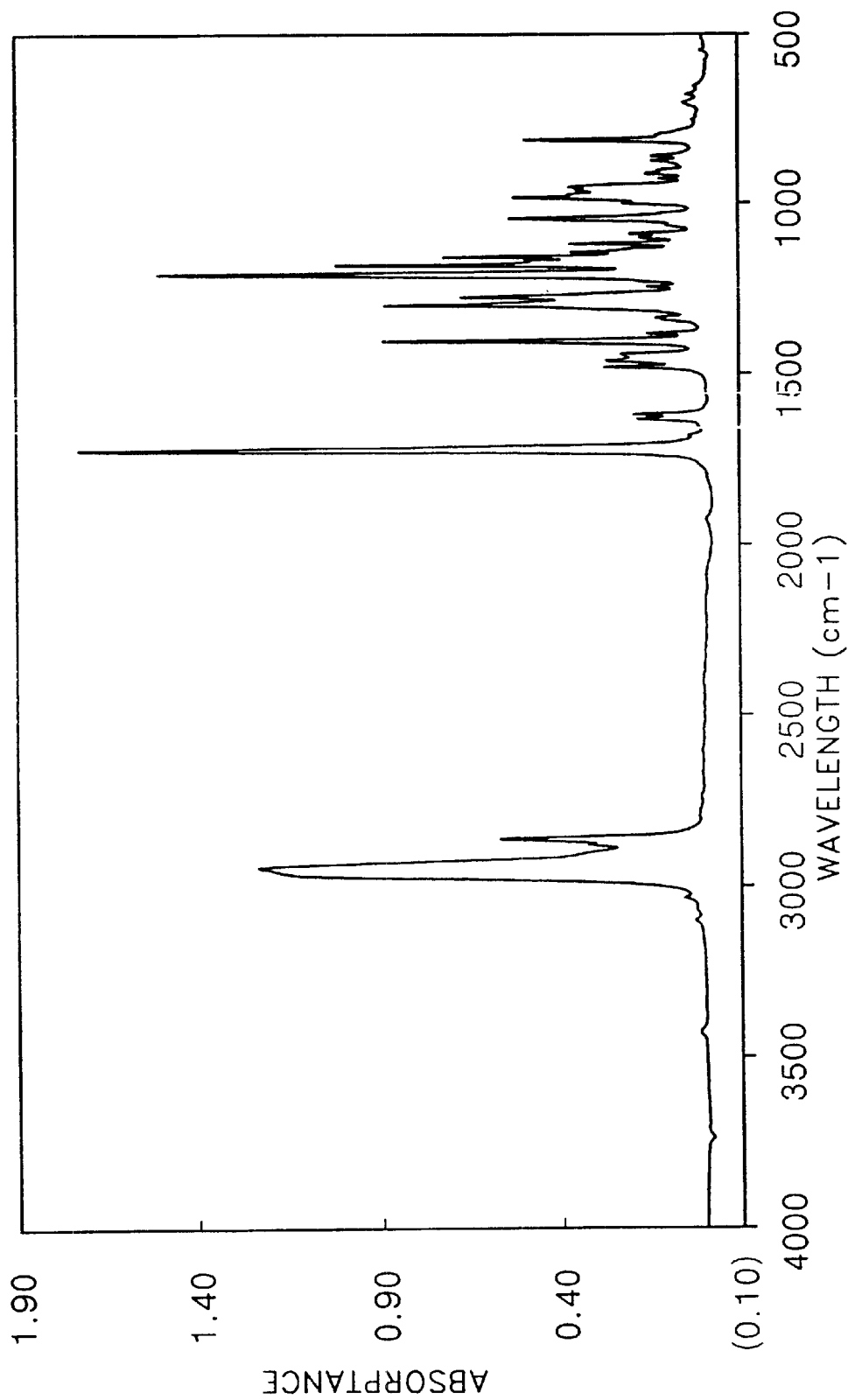
FIG. 2 is an FT-IR spectrum of 8-ethyl-8-tricyclodecanyl acrylate produced in Example 1 of the present invention.

8-Ethyl-8-tricyclodecanyl Acrylate a. Synthesis of 8-Ethyl-8-tricyclodecanol 440 ml of a solution of ethyl magnesium bromide (1.0 M) in tetrahydrofuran (THF) was diluted with 100 ml of anhydrous THF. Then, the solution was put into a 1 liter flask and then maintained at 0° C. Tricyclodecan-8-one (60 g, 0.4 mol) was dropped slowly using a dropping funnel and then the reaction was stirred at room temperature for about 12 hours. After completion of the reaction, excess THF was removed using a rotary evaporator and then the resultant product was poured into water. Then, the resultant product was neutralized with dilute sulfuric acid and extracted using diethyl ether and was then dried over magnesium sulfate. The obtained crude product was filtered by column chromatography (n-hexane:ethylacetate=8:1) to yield the desired product 8-ethyl-8-tricyclodecanol (yield: 70%).

b. Synthesis of 8-Ethyl-8-tricyclodecanyl Acrylate 8-ethyl-8-tricyclodecanol (36 g, 0.2 mol) and triethylamine (0.22 mol) were dissolved in 250 ml of THF and then acryloyl chloride (19 g, 0.21 mol) was added slowly thereto using a dropping funnel. Then, the reaction was stirred at room temperature for about 12 hours. After completion of the reaction, excess THF was removed using a rotary evaporator and then the resultant product was poured into water. Then, the resultant product was neutralized with dilute chloric acid and extracted using diethyl ether and was then dried over magnesium sulfate. The obtained crude product was filtered by column chromatography (n-hexane:ethylacetate=4:1) to yield the desired product 8-ethyl-8-tricyclodecanyl acrylate (yield: 80%). FIGS. 1 and 2 are NMR and FT-IR spectrums of the compound.

$^1$H-NMR (CDCl$_3$; ppm): 6.3 (1H, d), 6.1 (1H, dd), 5.7 (1H, d), 2.5 (1H, s), 2.2 (2H, m), 1.4 (2H, d), 0.8 (3H, t); FT-IR (NaCl; cm$^{-1}$): 2947, 2863, 1722, 1638, 1621, 1402, 1205.

EXAMPLE 2

8-Methyl-8-tricyclodecanyl Acrylate

The title compound was prepared in the same manner as in Example 1, except that methyl magnesium bromide was used instead of ethyl magnesium bromide (yield: 60%).

EXAMPLE 3

8-Ethyl-8-tricyclodecanyl Methacrylate

The title compound was prepared in the same manner as in Example 1, except that methacryloyl chloride was used instead of acryloyl chloride (yield: 65%).

EXAMPLE 4

8-Methyl-8-tricyclodecanyl Methacrylate

The title compound was prepared in the same manner as in Example 2, except that methacryloyl chloride was used instead of acryloyl chloride (yield: 68%).

8-alkyl-8-tricyclodecanyl (meth)acrylate according to the present invention can be produced in a high yield by an in-situ process to be advantageous for mass production of a commercial scale, and can be commercially used as various kinds of flame retardants because of its low chemical reactivity due to a bulky cyclodecanyl substituent.

What is claimed is:

1. A method of producing 8-alkyl-8-tricylcodecanyl (meth)acrylate represented by the formula:

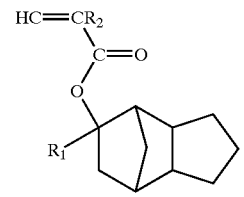

wherein R1 is methyl or ethyl and R2 is hydrogen or methyl, comprising the steps of:

a) synthesizing 8-alkyl-8-tricyclodecanol by reacting tricyclodecan-8-one with either an alkyl Grignard reagent or an alkyl lithium reagent; and b) synthesizing 8-ethyl-8-tricyclodecanyl acrylate by reacting the 8-alkyl-8-tricyclodecanol synthesized in the step a) with (meth)acryloyl chloride.

2. The method according to claim 1, wherein the Grignard reagent is either alkyl magnesium bromide or alkyl magnesium chloride.

3. The method according to claim 1, wherein if the alkyl is ethyl, ethyl magnesium bromide or ethyl magnesium chloride is used as the Grignard reagent.

* * * * *